United States Patent [19]

Esanu

[11] Patent Number: 4,581,362
[45] Date of Patent: Apr. 8, 1986

[54] 6-SUBSTITUTED FURO-(3,4-C)-PYRIDINE DERIVATIVES AND ANTI-DEPRESSANT COMPOSITIONS CONTAINING THE SAME

[75] Inventor: André Esanu, Paris, France

[73] Assignee: Societe de Conseils de Recherches et d'Applications Scientifiques (S.C.R.A.S.), France

[21] Appl. No.: 693,715

[22] Filed: Jan. 23, 1985

[30] Foreign Application Priority Data

Feb. 2, 1984 [GB] United Kingdom ............... 8402740

[51] Int. Cl.$^4$ .................. A61K 31/44; C07D 491/048
[52] U.S. Cl. ..................................... 514/302; 546/116
[58] Field of Search ................... 546/116; 424/256; 514/302

[56] References Cited

U.S. PATENT DOCUMENTS 4,383,998  5/1983  Esanu .................................. 424/256

OTHER PUBLICATIONS

Robert Morrison and Robert Boyd, "Organic Chemistry", 2nd Ed., Allyn and Bacon, Inc., 1966 (Boston).

Primary Examiner—Henry R. Jiles
Assistant Examiner—Bernard I. Dentz
Attorney, Agent, or Firm—Lucas & Just

[57] ABSTRACT

This invention relates to new 1,3-dihydro-6-(1-hydroxy-2-dimethylaminomethyl-allyl)-7-hydroxy-furo-(3,4-c)-pyridine derivatives of the general formula:

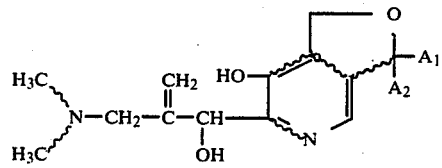

wherein, each of $A_1$ and $A_2$ independently, represents various substituents, to a process for the preparation of these compounds comprising reacting a 6-formyl-7-benzyloxy-furo-(3,4-c)-pyridine derivative of the general formula II

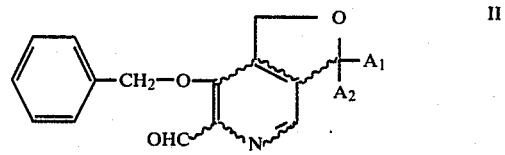

with 1-dimethylaminomethyl-vinylmagnesium bromide at the boil, in a non polar solvent and hydrolyzing the 7-benzyloxy group and to a therapeutic composition of matter, comprising as an essential ingredient therein, at least one of these compounds. The compounds according to the invention are of interest for their therapeutic activity, principally as anti-depressive agents.

2 Claims, No Drawings

6-SUBSTITUTED FURO-(3,4-C)-PYRIDINE DERIVATIVES AND ANTI-DEPRESSANT COMPOSITIONS CONTAINING THE SAME

This invention relates to new 6-(1-hydroxy-2-dimethyl-amino-methyl-allyl)-furo-(3,4-c)-pyridine derivatives, to a process for their preparation and to therapeutic compositions containing them.

The invention provides 1,3-dihydro-6-(1-hydroxy-2-dimethylaminomethyl-allyl)-7-hydroxy-furo-(3,4-c)-pyridine derivatives of the general formula:

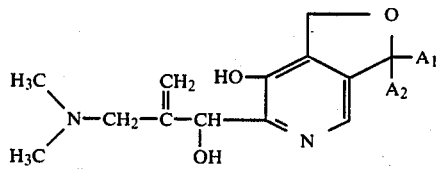

wherein, each of $A_1$ and $A_2$ independently, represents a hydrogen atom, a straight chain saturated or unsaturated hydrocarbon group having from 1 to 5 carbon atoms, a heterocyclic group having up to 6 ring atoms, a carbomonocyclic grup, a phenylalkyl group or a phenylalkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy groups has from 1 to 5 carbon atoms or α or β-alkoxy-N-pyrrolidinyl groups in which the alkoxy group has from 1 to 5 carbon atoms; and further provides pharmaceutically acceptable salts of such compounds.

The compounds according to the invention are of interest for their therapeutical activity, principally as antidepressive agents.

The invention also provides a process for the preparation of the said compounds, the process comprising reacting a 6-formyl-7-benzyloxy-furo-(3,4-c)-pyridine derivative of the general formula II

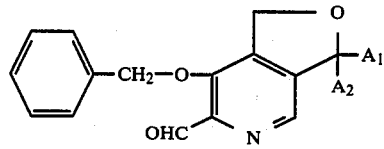

wherein $A_1$ and $A_2$ have the above meanings with 1-dimethylaminomethyl-vinylmagnesium bromide at the boil, in a non polar solvent such as tetrahydrofuran and hydrolysing the 7-benzyloxy group of the resultant intermediate by treatment with an acid.

To obtain the 6-formyl-7-benzyloxy-furo-(3,4-c)-pyridine derivative II the starting material is the compound III:

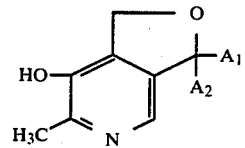

obtained by the method described in our U.S. Pat. No. 4,383,998 submitted to the following sequence of reactions:

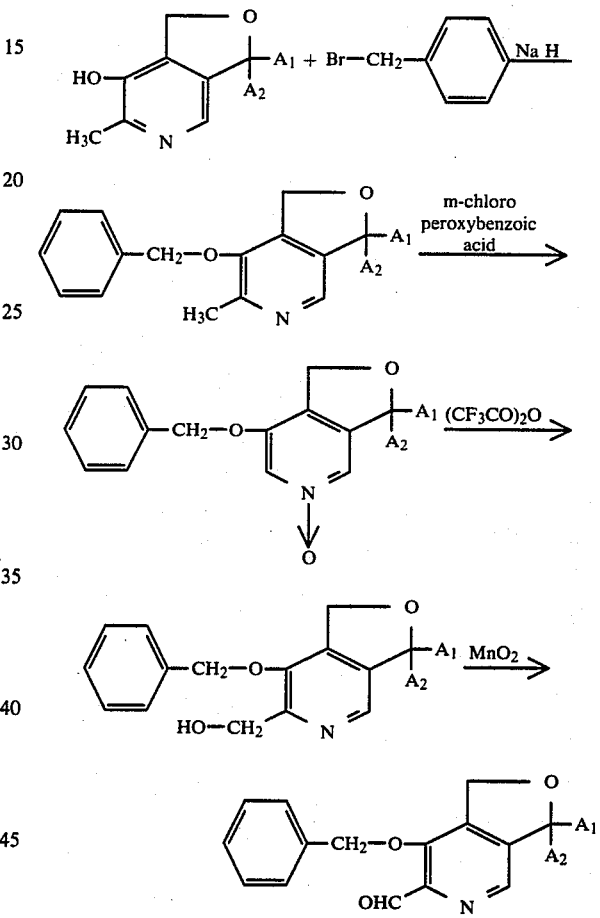

The invention further provides a therapeutical composition comprising a 1,3-dihydro-6-(1-hydroxy-2-dimethylamino-methyl-allyl)-furo-(3,4-c)-pyridine derivative of the general formula I as above defined or a pharmaceutically acceptable salt thereof in admixture with a therapeutically acceptable diluent or carrier.

The following examples illustrate the invention.

EXAMPLE 1

1,3-dihydro-3-methyl-6-(1-hydroxy-2-dimethylaminomethyl-allyl)-7-hydroxy-furo-(3,4-c)-pyridine (a) Preparation of the organomagnesium reagent In a two liter reactor fitted with warming, cooling and stirring means were poured, under nitrogen circulation, 19.4 g (0.8 mol) of magnesium, and 100 ml of tetrahydrofuran, preferably distilled on lithium aluminium hydride. The mixture was refluxed.

There was then slowly added 132 g (0.8 mol) of 3-dimethylamino-2-bromo-1-propylene. No external heating was applied, the reflux being maintained and controlled by the addition of this compound. At the end of the addition, one liter of distilled tetrahydrofuran was added. The mixture was refluxed for two hours and then cooled to 10° C.

(b) Reaction

To the reaction mixture from the previous step was slowly added, under stirring, 107.6 g (0.4 mol) of 1,3-dihydro-3-methyl-6-formyl-7-benzyloxy-furo-(3,4-c)-pyridine. The temperature reached about 25° C. at the end of the addition. Stirring was maintained overnight at room temperature. The mixture was then cooled to 0° C. and 250 ml of water saturated with ammonium chloride and 250 ml of diethyl ether were added to it. After stirring for 15 minutes at room temperature there was obtained a two-phase mixture with an oil supernatant.

The mixture was separated and the aqueous phase was extracted twice with 250 ml aliquots of diethyl ether. The extracts were added to the oily phase, which had been washed with water three times. The oily phase was then dried on magnesium sulphate, treated with carbon black, concentrated to dryness and extracted twice with 250 ml of diisopropylether. The extracts were filtered, concentrated (reduction to ¼ of initial volume) and cooled overnight, leading to a precipitate, which was separated and washed with diisopropylether. Yield 104 g (73%).

(c) Debenzylation

Into the above reactor were poured the product of the previous step and 700 ml of hydrochloric acid. The mixture was stirred, warmed to 55° C., maintained at that temperature for three hours, and then cooled to 0° C. After addition of water, neutralisation with sodium hydroxide and saturation with sodium chloride, the mixture was extracted three times with 500 ml aliquots of chloroform. The extracts were washed with water, dried on magnesium sulphate, filtered and evaporated to dryness. The residue was recrystallised from methanol. Yield 90.5 g (92%) of a product melting at 200°–205° C. (Tottoli), with decomposition, the analysis of which showed a good correspondence with the formula $C_{14}H_{20}N_2O_3.2HCl$. The overall yield was 67%.

The preparation of the other compounds of the invention follows the same process except that, in step (b), the starting material is different; the following examples will, accordingly refer to example 1 and only mention the new starting material, the overall yield and the characteristics of the compound obtained.

EXAMPLE 2

1,3-dihydro-3-propyl-6-(1-hydroxy-2-dimethylaminomethyl-allyl)-7-hydroxy-furo-(3,4-c)-pyridine The method of example 1 was repeated, but starting with 119 g (0.4 mol) of 1,3-dihydro-3-propyl-6-formyl-7-benzyloxy-furo-(3,4-c)-pyridine. Yield 89 g (61%) of a product melting at 187°–194° C. (Tottoli), with decomposition, the analysis of which showed a good correspondence with the formula $C_{16}H_{24}N_2O_3,2HCl$.

EXAMPLE 3

1,3-dihydro-3-cyclohexyl-6-(1-hydroxy-2-dimethylaminomethyl-allyl)-7-hydroxy-furo-(3,4-c)-pyridine The method of example 1 was repeated, but starting with 135 g (0.4 mol) of 1,3-dihydro-3-cyclohexyl-6-formyl-7-benzyloxy-furo-(3,4-c)-pyridine. Yield 92 g (57%) of a product melting at 180°–184° C. (Tottoli), with decomposition, the analysis of which showed a good correspondence with the formula $C_{19}H_{28}N_2O_3,2HCl$.

EXAMPLE 4

1,3-dihydro-3-phenyl-6-(1-hydroxy-2-dimethylaminomethyl-allyl)-7-hydroxy-furo-(3,4-c)-pyridine The method of example 1 was repeated, but starting with 135 g (0.4 mol) of 1,3-dihydro-3-phenyl-6-formyl-7-benzyloxy-furo-(3,4-c)-pyridine. Yield 77 g (48%) of a product melting at 210°–215° C. (Tottoli), with decomposition, the analysis of which showed a good correspondence with the formula $C_{19}H_{22}N_2O_3,2HCl$.

EXAMPLE 5

1,3-dihydro-3-p-chlorophenyl-6-(1-hydroxy-2-dimethylaminomethyl-allyl)-7-hydroxy-furo-(3,4-c)-pyridine The method of example 1 was repeated, but starting with 146 g (0.4 mol) of 1,3-dihydro-3-p-chlorophenyl-6-formyl-7-benzyloxy-furo-(3,4-c)-pyridine. Yield 95 g (55%) of a product melting at 195°–200° C. (Tottoli), with decomposition, the analysis of which showed a good correspondence with the formula $C_{19}H_{21}ClN_2O_3.2HCl$.

EXAMPLE 6

1,3-dihydro-3-(2,3-dichlorophenyl)-6-(1-hydroxy-2-dimethylaminomethyl-allyl)-7-hydroxy-furo-(3,4-c)-pyridine The method of example 1 was repeated, but starting with 160 g (0.4 mol) of 1,3-dihydro-3-(2,3-dichlorophenyl)-6-formyl-7-benzyloxy-furo-(3,4-c)-pyridine. Yield 82 g (44%) of a product melting at 180°–184° C. (Tottoli), with decomposition, the analysis of which showed a good correspondence with the formula $C_{19}H_{20}Cl_2N_2O_3.2HCl$.

EXAMPLE 7

1,3-dihydro-3-p-fluorophenyl-6-(1-hydroxy-2-dimethylaminomethyl-allyl)-7-hydroxy-furo-(3,4-c)-pyridine The method of example 1 was repeated, but starting with 140 g (0.4 mol) of 1,3-dihydro-3-p-fluorophenyl-6-formyl-7-benzyloxy-furo-(3,4-c)-pyridine. Yield 85 g (51%) of a product melting at 198° C. (Tottoli), with decomposition, the analysis of which showed a good correspondence with the formula $C_{19}H_{21}FN_2O_3.2HCl$.

EXAMPLE 8

1,3-dihydro-3-p-toluyl-6-(1-hydroxy-2-dimethylaminomethyl-allyl)-7-hydroxy-furo-(3,4-c)-pyridine The method of example 1 was repeated, but starting with 138 g (0.4 mol) of 1,3-dihydro-3-p-toluyl-6-formyl-7-benzyloxy-furo-(3,4-c)-pyridine. Yield 81 g (49%) of a product melting at 203°–207° C. (Tottoli), with decomposition, the analysis of which showed a good correspondence with the formula $C_{20}H_{24}N_2O_3.2HCl$.

EXAMPLE 9

1,3-dihydro-3-p-methoxyphenyl-6-(1-hydroxy-2-dimethylaminomethyl-allyl)-7-hydroxy-furo-(3,4-c)-pyridine The method of example 1 was repeated, but starting with 145 g (0.4 mol) of 1,3-dihydro-3-p-methoxyphenyl-6-formyl-7-benzyloxy-furo-(3,4-c)-pyridine. Yield 86 g (50%) of a product melting at 169°–170° C. (Tottoli), the analysis of which showed a good correspondence with the formula $C_{20}H_{24}N_2O_4.2HCl$.

EXAMPLE 10

1,3-dihydro-3-m-trifluoromethylphenyl-6-(1-hydroxy-2-dimethylaminomethyl-allyl)-7-hydroxy-furo-(3,4-c)-pyridine The method of example 1 was repeated, but starting with 161 g (0.4 mol) of 1,3-dihydro-3-m-trifluoromethylphenyl-6-formyl-7-benzyloxy-furo-(3,4-c)-pyridine. Yield 102 g (54%) of a product melting at 217°–223° C. (Tottoli), with decomposition, the analysis of which showed a good correspondence with the formula $C_{20}H_{21}F_3N_2O_3.2HCl$.

EXAMPLE 11

1,3-dihydro-3-p-(diethylaminoethoxy-phenyl)-6-(1-hydroxy-2-dimethylaminomethyl-allyl)-7-hydroxy-furo-(3,4-c)-pyridine The method of example 1 was repeated, but starting with 178 g (0.4 mol) of 1,3-dihydro-3-p-(diethylaminoethoxy-phenyl)-6-formyl-7-benzyloxy-furo-(3,4-c)-pyridine. Yield 76 g (37%) of a product melting at 158°–160° C. (Tottoli), the analysis of which showed a good correspondence with the formula $C_{25}H_{35}N_3O_4.2HCl$.

EXAMPLE 12

1,3-dihydro-3-p-(pyrrolidinylethoxy-phenyl)-6-(1-hydroxy-2-dimethylaminomethyl-allyl)-7-hydroxy-furo-(3,4-c)-pyridine The method of example 1 was repeated, but starting with 178 g (0.4 mol) of 1,3-dihydro-3-p-(pyrrolidinylethoxy-phenyl)-6-formyl-7-benzyloxy-furo-(3,4-c)-pyridine. Yield 70 g (34%) of a product melting at 173° C. (Tottoli), the analysis of which showed a good correspondence with the formula $C_{25}H_{33}N_3O_4.2HCl$.

EXAMPLE 13

1,3-dihydro-3-methyl-3-n-pentyl-6-(1-hydroxy-2-dimethylaminomethyl-allyl)-7-hydroxy-furo-(3,4-c)-pyridine The method of example 1 was repeated, but starting with 136 g (0.4 mol) of 1,3-dihydro-3-methyl-3-n-pentyl-6-formyl-7-benzyloxy-furo-(3,4-c)-pyridine. Yield 94 g (58%) of a product melting at 187°–191° C. (Tottoli), with decomposition, the analysis of which showed a good correspondence with the formula $C_{19}H_{30}N_2O_3.2HCl$.

EXAMPLE 14

1,3-dihydro-3-methyl-3-phenyl-6-(1-hydroxy-2-dimethylaminomethyl-allyl)-7-hydroxy-furo-(3,4-c)-pyridine The method of example 1 was repeated, but starting with 138 g (0.4 mol) of 1,3-dihydro-3-methyl-3-phenyl-6-formyl-7-benzyloxy-furo-(3,4-c)-pyridine. Yield 104 g (63%) of a product melting at 178°–179° C. (Tottoli), the analysis of which showed a good correspondence with the formula $C_{20}H_{24}N_2O_3.2HCl$.

EXAMPLE 15

1,3-dihydro-3-methyl-3-α-thienyl-6-(1-hydroxy-2-dimethylaminomethyl-allyl)-7-hydroxy-furo-(3,4-c)-pyridine The method of example 1 was repeated, but starting with 140 g (0.4 mol) of 1,3-dihydro-3-methyl-3-α-thienyl-6-formyl-7-benzyloxy-furo-(3,4-c)-pyridine. Yield 77 g (46%) of a product melting at 169°–175° C. (Tottoli), with decomposition, the analysis of which showed a good correspondence with the formula $C_{18}H_{22}SN_2O_3.2HCl$.

EXAMPLE 16

1,3-dihydro-3-ethyl-3-m-trifluoromethylphenyl-6-(1-hydroxy-2-dimethylaminomethyl-allyl)-7-hydroxy-furo-(3,4-c)-pyridine The method of example 1 was repeated, but starting with 172 g (0.4 mol) of 1,3-dihydro-3-ethyl-3-m-trifluoromethylphenyl-6-formyl-7-benzyloxy-furo-(3,4-c)-pyridine. Yield 117 g (59%) of a product melting at 185° C. (Tottoli), the analysis of which showed a good correspondence with the formula $C_{22}H_{25}F_3N_2O_3.2HCl$.

EXAMPLE 17

1,3-dihydro-3-ethyl-3-α-furyl-6-(1-hydroxy-2-dimethylaminomethyl-allyl)-7-hydroxy-furo-(3,4-c)-pyridine The method of example 1 was repeated, but starting with 140 g (0.4 mol) of 1,3-dihydro-3-ethyl-3-α-furyl-6-formyl-7-benzyloxy-furo-(3,4-c)-pyridine. Yield 68 g (41%) of a product melting at 164°–169° C. (Tottoli), with decomposition, the analysis of which showed a good correspondence with the formula $C_{19}H_{24}N_2O_4.2HCl$.

EXAMPLE 18

1,3-dihydro-3-phenyl-3-p-ethoxyphenyl-6-(1-hydroxy-2-dimethylaminomethyl-allyl)-7-hydroxy-furo-(3,5-c)-pyridine The method of example 1 was repeated, but starting with 180 g (0.4 mol) of 1,3-dihydro-3-phenyl-3-p-ethoxyphenyl-6-formyl-7-benzyloxy-furo-(3,4-c)-pyridine. Yield 99 g (48%) of a product melting at 148°–149° C. (Tottoli), the analysis of which showed a good correspondence with the formula $C_{27}H_{30}N_2O_4.2HCl$.

EXAMPLE 19

1,3-dihydro-3,3-di-p-fluorophenyl-6-(1-hydroxy-2-dimethylaminomethyl-allyl)-7-hydroxy-furo-(3,4-c)-pyridine The method of example 1 was repeated, but starting with 178 g (0,4 mol) of 1,3-dihydro-3,3-di-p-fluorophenyl-6-formyl-7-benzyloxy-furo-(3,4-c)-pyridine. Yield 115 g (56%) of a product melting at 175° C. (Tottoli), the analysis of which showed a good correspondence with the formula $C_{25}H_{24}F_2N_2O_3.2HCl$.

EXAMPLE 20

1,3-dihydro-3-α-furyl-3-p-thiomethylphenyl-6-(1-hydroxy-2-dimethylaminomethyl-allyl)-7-hydroxy-furo-(3,4-c)-pyridine The method of example 1 was repeated, but starting with 177 g (0.4 mol) of 1,3-dihydro-3-α-furyl-3-p-thiomethylphenyl-6-formyl-7-benzyloxy-furo-(3,4-c)-pyridine. Yield 82 g (40%) of a product melting at 143°–151° C. (Tottoli), with decomposition, the analysis of which showed a good correspondence with the formula $C_{24}H_{26}SN_2O_4.2HCl$.

TOXICITY

None of the prepared compounds revealed an important per os toxicity: $LD_{50}$ was comprised between 0.8 and 1.2 g/kg on rats and between 0.7 and 1 g/kg for mice.

PHARMACOLOGY

The activity of the compounds of the invention has been evidenced by various tests, three of which are reported in details as follows.

I. Lethality provoked by Yohimbine HCl in mice

This test was conducted on batches of 10 male CD-1 (Charles River) mice. Each treated mouse received 0.25 ml/20 g of a suspension containing the tested dose of compound. One hour after the administration, the mice were injected subcutaneously 30 mg/kg of Yohimbine HCl. Percentage of death (L) was determined 18 hours after this injection. A Yohimbine HCl control batch was provided for each compound. The results are reported in the table No. I.

II. Antagonism against catalepsy induced by haloperidol

This experiment was conducted in comparison with two reference compounds, Imipramine and 5-hydroxytrytophane on male Wistar rats of 140/170 g in batches of each 6 rats.

IP administration of haloperidol at 5 mg/kg induces catalepsy. Further oral administration of the tested compounds one hour after haloperidol injection has an adverse action against catalepsy.

Eight of the compounds of the invention were tested at various doses (one batch for each dose of each compound). Action on catalepsy was appreciated 1,2,3,4 and 5 hours after the administration of the tested compounds by placing anterior paws of the rats on a metal bar located at 10 cm above table level (test performed in a noiseless room at 22° C.); if the rat was able to stay for 20 seconds, the score was 1 point; for 40 seconds the score was 2 points and so on up to 100 seconds for 5 points. Average values were calculated for each batch together with the corresponding percentage of antagonism.

The results are reported in the table No. II.

III. Despair test on mice

This experiment was conducted on male mice CD-1 (Charles River) in batches of each 10 mice in comparison with Maprotiline as a reference compound. One hour before the test, the mice received in a dose of 0.4 ml/20 g of suspension, the appropriate dose in mg/kg of the tested compounds.

The mice were placed in plexiglass cylinder (height 25 cm, diameter 10 cm) containing water at 22° C. The measure of immobility period was effected between the 2nd and 6th minute. There was one control batch for each compound and one batch per tested dose.

The results are reported in the table No. III wherein A stands for the average immobility period and B stands for the % of variation with regard to control.

PRESENTATION

Posology

More commonly used forms in human therapy comprise tablets or gelatine capsules containing 0.1 g of active ingredient per dosage unit or phials containing the same amount in a dissolved or suspended form for IV injection.

Usual posology is up to 0.5 g/day for at least two weeks, for oral forms or up to 0.2 g/day for at least one week for the injectable form, this treatment being followed by at least one week of oral administration.

TABLE I

| Products | Doses | L |
|---|---|---|
| Yohimbine HCl | 30 mg/kg SC | 20% |
| Ex. 1 | 30 mg/kg PO | 40% |
|  | 100 mg/kg PO | 60% |
| Yohimbine HCl | 30 mg/kg SC | 20% |
| Ex. 4 | 30 mg/kg PO | 50% |
|  | 60 mg/kg PO | 60% |
| Yohimbine HCl | 30 mg/kg SC | 20% |
| Ex. 5 | 10 mg/kg PO | 60% |
|  | 30 mg/kg PO | 60% |
| Yohimbine HCl | 30 mg/kg SC | 20% |
| Ex. 7 | 3 mg/kg PO | 50% |
|  | 10 mg/kg PO | 50% |
| Yohimbine HCl | 30 mg/kg SC | 20% |
| Ex. 11 | 30 mg/kg PO | 30% |
|  | 100 mg/kg PO | 90% |
| Yohimbine HCl | 30 mg/kg SC | 20% |
| Ex. 12 | 30 mg/kg PO | 40% |
|  | 60 mg/kg PO | 50% |
| Yohimbine HCl | 30 mg/kg SC | 20% |
| Ex. 17 | 30 mg/kg PO | 80% |
|  | 100 mg/kg PO | 90% |
| Yohimbine HCl | 30 mg/kg SC | 20% |
| Ex. 20 | 30 mg/kg PO | 50% |
|  | 100 mg/kg PO | 60% |

TABLE II

| Examples | Dose mg/kg per os | Antagonism in % after: (hours) | | | | |
|---|---|---|---|---|---|---|
|  |  | 1 h | 2 h | 3 h | 4 h | 5 h |
| Imipramine | 15 | 100 | 52.3 | 42.3 | 48.2 | 50 |
|  | 60 | 68.7 | 76.1 | 42.3 | 31 | 33.3 |
| 5 HTP | 30 | 53.3 | 42.8 | 20.6 | 13.8 | 16.6 |
|  | 100 | 33.3 | 46.4 | 31 | 13.8 | 16.6 |
| Ex. 1 | 30 | 60 | 63.6 | 44 | 35.7 | 25 |
|  | 100 | 100 | 50 | 54.5 | 46.4 | 40 |
| Ex. 4 | 1 | 58.3 | 70 | 50 | 33.7 | 16.6 |
|  | 3 | 100 | 75 | 80 | 56.6 | 50 |
| Ex. 5 | 10 | 100 | 100 | 78 | 78 | 64 |
|  | 30 | 37 | 75 | 46 | 50 | 47 |
| Ex. 7 | 3 | 0 | 58.3 | 60.7 | 41.4 | 48.2 |
|  | 10 | 28.5 | 79.1 | 78.6 | 79.3 | 72.4 |
| Ex. 11 | 10 | 50 | 100 | 60 | 53.3 | 53.3 |
|  | 30 | 100 | 80.7 | 62.9 | 55.1 | 41.4 |
| Ex. 12 | 10 | 0 | 30.4 | 37 | 43.3 | 46.6 |
|  | 30 | 0 | 30.4 | 40.7 | 46.6 | 40 |
| Ex. 17 | 3 | 100 | 54.5 | 48.3 | 24.1 | 26.6 |
|  | 10 | 100 | 59 | 51.7 | 24.1 | 40 |
| Ex. 20 | 10 | 93.3 | 76 | 70 | 60.7 | 55.1 |
|  | 30 | 100 | 68 | 50 | 54.5 | 51.7 |

TABLE III

| Examples | Doses | A | B |
|---|---|---|---|
| Control | — | 204 |  |
| Maprotiline | 10 mg/kg PO | 156.3 | −23.4 NS |
|  | 30 mg/kg PO | 143.3 | −29.7* |
|  | 100 mg/kg PO | 86.5 | −57.6*** |
| Control | — | 203.8 |  |
| Ex. 1 | 1 mg/kg PO | 157.4 | −25* |
|  | 3 mg/kg PO | 133.1 | −34.7** |
|  | 10 mg/kg PO | 82.1 | −59.6*** |
| Control | — | 198.3 |  |
| Ex. 4 | 10 mg/kg PO | 136.4 | −31.2* |
|  | 30 mg/kg PO | 135.6 | −31.6* |
|  | 100 mg/kg PO | 138.3 | −30.3* |
| Control | — | 207.1 |  |
| Ex. 5 | 10 mg/kg PO | 145.4 | −29.8* |
|  | 30 mg/kg PO | 124.4 | −39.9** |
|  | 100 mg/kg PO | 86.7 | −58.1*** |
| Control | — | 189.9 |  |
| Ex. 7 | 3 mg/kg PO | 137 | −27.9* |
|  | 10 mg/kg PO | 135.2 | −28.8* |
|  | 30 mg/kg PO | 101.1 | −46.6** |
| Control | — | 200.3 |  |
| Ex. 11 | 10 mg/kg PO | 144.6 | −27.8* |
|  | 30 mg/kg PO | 136.6 | −31.8** |
|  | 100 mg/kg PO | 118.1 | −41.4** |

TABLE III-continued

| Examples | Doses | A | B |
|---|---|---|---|
| Control | — | 148.5 | |
| Ex. 12 | 30 mg/kg PO | 106.1 | −28.6* |
| | 100 mg/kg PO | 99.0 | −33.3* |
| | 300 mg/kg PO | 77.4 | −47.9** |
| Control | — | 200 | |
| Ex. 17 | 10 mg/kg PO | 175.2 | −12.4 NS |
| | 30 mg/kg PO | 142.7 | −28.6** |
| | 100 mg/kg PO | 155.4 | −22.3 NS |
| Control | — | 213.5 | |
| Ex. 20 | 10 mg/kg PO | 183.4 | −14.1 NS |
| | 30 mg/kg PO | 86.3 | −59.6** |
| | 60 mg/kg PO | 97.2 | −54.5** |

I claim:

1. A 1,3-dihydro-6-(1-hydroxy-2-dimethylaminomethyl-allyl)-7-hydroxy-furo-(3,4-c)-pyridine derivative of the formula:

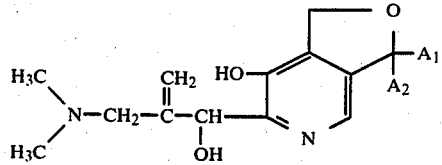

wherein, each of $A_1$ and $A_2$ independently, represents a hydrogen atom, a straight chain saturated or unsaturated hydrocarbon group having from 1 to 5 carbon atoms, a thienyl, furyl, cyclohexyl, or phenyl group, a phenylalkyl group or a phenylalkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy groups has from 1 to 5 carbon atoms or $\alpha$ or $\beta$-alkoxy-N-pyrrolidinyl groups in which the alkoxy group has from 1 to 5 carbon atoms; and pharmaceutically acceptable salts thereof.

2. A therapeutic composition of matter, comprising as an essential ingredient therein an amount sufficient to act as an anti-depressant, at least one compound of claim 1 together with a pharmaceutically acceptable carrier.

* * * * *

UNITED STATES PATENT AND TRADEMARK OFFICE
CERTIFICATE OF CORRECTION

PATENT NO. : 4,581,362
DATED : April 8, 1986
INVENTOR(S) : Andre Esanu

It is certified that error appears in the above-identified patent and that said Letters Patent is hereby corrected as shown below:

Column 1, line 28, change "grup" to --group--.

Column 6, line 30, change "(3,5-c)" to --(3,4-c)--.

Claim 2, line 3, after "anti-depressant", delete "," and insert --of--.

Signed and Sealed this

Ninth Day of September 1986

[SEAL]

Attest:

DONALD J. QUIGG

Attesting Officer     Commissioner of Patents and Trademarks